United States Patent
Zach et al.

(10) Patent No.: US 9,733,201 B2
(45) Date of Patent: Aug. 15, 2017

(54) THERMAL AGE TRACKING SYSTEM AND METHOD

(71) Applicants: Juergen J. Zach, Menlo Park, CA (US); Jim Beres, Menlo Park, CA (US); Erik Olson, Albuquerque, NM (US)

(72) Inventors: Juergen J. Zach, Menlo Park, CA (US); Jim Beres, Menlo Park, CA (US); Erik Olson, Albuquerque, NM (US)

(73) Assignee: Pentair Thermal Management LLC, Redwood City, CA (US)

( * ) Notice: Subject to any disclaimer, the term of this patent is extended or adjusted under 35 U.S.C. 154(b) by 864 days.

(21) Appl. No.: 14/081,722

(22) Filed: Nov. 15, 2013

(65) Prior Publication Data

US 2015/0142343 A1   May 21, 2015

(51) Int. Cl.
*G01N 27/00* (2006.01)
*G01N 25/00* (2006.01)
*G01R 31/02* (2006.01)
*G01R 31/00* (2006.01)

(52) U.S. Cl.
CPC .............. *G01N 27/00* (2013.01); *G01N 25/00* (2013.01); *G01R 31/003* (2013.01); *G01R 31/021* (2013.01)

(58) Field of Classification Search
CPC ..................................................... G01N 27/00
USPC .......................................................... 702/57
See application file for complete search history.

(56) References Cited

U.S. PATENT DOCUMENTS

| | | | |
|---|---|---|---|
| 4,698,583 | A | 10/1987 | Sandberg |
| 5,122,641 | A | 6/1992 | DeChurch |
| 5,568,371 | A | 10/1996 | Pitel et al. |
| 5,574,440 | A | 11/1996 | Kurtz |
| 5,578,931 | A | 11/1996 | Russell et al. |
| 6,002,561 | A | 12/1999 | Dougherty |

(Continued)

FOREIGN PATENT DOCUMENTS

EP    2637473 A1    9/2013

OTHER PUBLICATIONS

Jovan M. Knezevic and Vladimir A. Katic, The Hybrid Method for On-line Harmonic Analysis, dated 2011, pp. 1-6.

(Continued)

*Primary Examiner* — Ricky Ngon
(74) *Attorney, Agent, or Firm* — Quarles & Brady LLP

(57) ABSTRACT

Embodiments of the invention provide systems and methods for tracking the thermal age of a self-regulating heating cable. Over a time period, current and voltage data for a cable signal are collected, from which spectral information is extracted. The spectral information has a frequency component and an amplitude component. The cable signal is processed to extract a line frequency signature that includes the electrical system's line current frequency and at least some of its harmonics. A ratio of the amplitudes of at least two of the odd harmonics of the line current frequency is calculated. The ratio is compared to an aging curve indicating the thermal age of the cable as a function of the odd-harmonic ratios. The curve may be obtained in a laboratory setting or in the field by characterizing a cable with zero hours of use. The characterizing may include aging the cable to determine the curve.

18 Claims, 7 Drawing Sheets

(56) References Cited

U.S. PATENT DOCUMENTS

| | | | |
|---|---|---|---|
| 6,288,372 | B1 | 9/2001 | Sandberg et al. |
| 6,400,258 | B1 | 6/2002 | Parker |
| 6,751,528 | B1 | 6/2004 | Dougherty |
| 7,391,218 | B2 | 6/2008 | Kojori et al. |
| 7,710,176 | B2 | 5/2010 | Yang |
| 2004/0232919 | A1* | 11/2004 | Lacey ................ G01R 31/11 324/533 |
| 2005/0247700 | A1* | 11/2005 | Kochman ............ H05B 3/56 219/544 |
| 2006/0212281 | A1 | 9/2006 | Mathews, Jr. et al. |
| 2008/0229120 | A1* | 9/2008 | Diab ................... H04L 12/66 713/300 |
| 2009/0119073 | A1 | 5/2009 | Bourgeois et al. |
| 2009/0220188 | A1 | 9/2009 | Bremnes |
| 2009/0281740 | A1* | 11/2009 | Stoupis .............. G01R 31/024 702/58 |
| 2010/0097733 | A1 | 4/2010 | Tomimbang |
| 2011/0218790 | A1* | 9/2011 | Algaonkar .......... G01K 11/32 703/13 |
| 2012/0109288 | A1 | 5/2012 | Bolling |
| 2014/0103938 | A1* | 4/2014 | Jones ................. G01R 31/021 324/511 |
| 2014/0305930 | A1* | 10/2014 | Heizer ................ G08C 17/02 219/539 |

OTHER PUBLICATIONS

T. Messikh, S. Mekhilef, and N. A. Rahim, Adaptive Notch Filter for Harmonic Current Mitigation, International Journal of Electrical and Computer Engineering, dated 2008, pp. 1-7.

\* cited by examiner

THERMAL AGE TRACKING SYSTEM AND METHOD

BACKGROUND

Self-regulating heating cables have an inherent useful lifetime, due to gradual changes in their materials as a result of exposure to environmental temperatures. Over time, the power output of heating cables diminishes, until the heating cables no longer efficiently heat their surroundings as intended and must be replaced. The diminishing of the power output of the heating cable relative to the initial power output is referred to as aging, and is a major concern in industry. All lifetime exposure, whether generated internally by the heater itself or received externally through the environmental conditions at the deployment site, has a cumulative aging effect on the heater. These environmental conditions include, but are not limited to, thermal oxidation of the core polymer material due to normal operation at an ambient temperature, degradation of the electrical contacts, mechanical damage or excessive heating beyond rated specifications which can lead to partial melting of the polymer material.

The most important aging mechanism is thermal oxidation of the core polymer material, which is an inherent property of self-regulating heaters operated under any conditions. This thermal oxidation mechanism will herein be described as "thermal aging". Thermal aging might be expressed through the percentage of the remaining power output of the heater relative to the original power output. The power output due to this mechanism versus time and exposure temperature is described by an Arrhenius-law equation:

$$\text{Power} = \text{Power}_0 * \exp\{(A - B * \text{time} * \exp(-C/\text{Temperature}))\},$$

where A, B and C are material constants specific to a certain type of heating cable, "Temperature" refers to the temperature in degrees Kelvin of the heating cable, "time" is the exposure time to that temperature, and Power and $\text{Power}_0$, respectively, refer to the power output in Watts of the heater after the exposure time and at initial installation. However, in many real applications, heaters are not exposed to constant temperatures at all times. Rather, the temperature can fluctuate to include very high temperatures for limited times, particularly in industrial applications. Because the exposure temperatures over time may be unknown, it is usually not possible to accurately predict the thermal aging of a heater in a certain application. It is therefore important to track the thermal age of a heating cable while installed. Thermal age mustn't be confused with the actual or installed age of the heater, but contains the integrated temperature history to which it was exposed over time. The reason for the diminished power output is an increase in the cable's resistivity that results from thermal aging. Hence, in principle, measurements of resistivity or power could serve as an indicator of thermal aging. However, the measurement loses its value as an indicator if the sample is cut, spliced, damaged or otherwise changed, since such measurements are referenced to an initial baseline measurement taken. More importantly, in order to be able to use simple power or resistivity measurements conducted under deployment conditions to determine the thermal age of the heating cable, the complete temperature profile along the cable installation would have to be known, which would defeat the purpose of installing a self-regulating heating cable, which self-regulates its power output to the temperature profile. Further, a resistivity measurement is only meaningful if the heater power output has reached thermal equilibrium; resistivity measured shortly after powering up the heater is confounded by an inrush effect.

In order for customers at deployment sites to better plan their schedule for heating cable replacement, an improved material-characteristic-based thermal age indicator is needed which does not require specific knowledge of the history of a particular deployed heating cable. The indicator should be inexpensive and non-invasive. In particular, it would be advantageous to utilize in situ measurements of heating cable characteristics, such as voltage and current, that may already be monitored by a controller for other purposes.

SUMMARY

Some embodiments of the invention provide a method of tracking thermal age of a heating cable. The method can include collecting a cable signal generated by passing a line current through the heating cable and extracting spectral information from the cable signal. The spectral information can include a line frequency, one or more harmonic frequencies of the line frequency, and an amplitude component for each of the line frequency and harmonic frequencies. The method can further include calculating one or more measured functional dependencies between one or more pairs of the harmonic frequency amplitudes, and comparing one or more of the measured functional dependencies to one or more stored harmonic functional dependencies that correlate to a thermal aging curve to determine the heating cable's current location on the thermal aging curve.

Some embodiments of the invention provide a method of tracking thermal age of a heating cable having a cable type. The method can include collecting a cable signal generated by passing a line current through the heating cable and extracting spectral information from the cable signal. The spectral information can include a line frequency, one or more harmonic frequencies of the line frequency, and an amplitude component for each of the line frequency and harmonic frequencies. The method can further include calculating one or more measured functional dependencies of one or more pairs of the harmonic frequency amplitudes, and determining the thermal age of the heating cable by comparing one or more of the measured functional dependencies to characterization data of the cable type.

Some embodiments of the invention provide another method of tracking thermal age of a heating cable having a cable type. The method can include characterizing the cable type to obtain a thermal aging curve and a subset of stored functional dependencies of harmonic frequency amplitudes that correlate to locations on the thermal aging curve. The method can further include collecting a cable signal generated by passing a line current through the heating cable and extracting spectral information from the cable signal. The spectral information can include a line frequency, one or more harmonic frequencies of the line frequency, and an amplitude component for each of the line frequency and harmonic frequencies. The method can further include calculating one or more measured functional dependencies of one or more pairs of the harmonic frequency amplitudes, and comparing one or more of the measured functional dependencies to one or more of the stored functional dependencies to determine the heating cable's current location on the thermal aging curve.

Some embodiments of the invention provide a system for tracking thermal age of a deployed heating cable having a cable type. The system can include a detection circuit in electrical communication with the heating cable. The detection circuit can be configured to collect a cable signal of the heating cable, the cable signal being generated by passing a line current through the heating cable. The system can further include a control unit in electrical communication with the detection circuit. The control unit can receive the cable signal from the detection circuit and can be configured to extract spectral information from the cable signal. The spectral information can include a line frequency, one or more harmonic frequencies of the line frequency, and an amplitude component for each of the line frequency and harmonic frequencies. The control unit can be further configured to calculate one or more measured functional dependencies of one or more pairs of the harmonic frequency amplitudes, and to compare one or more of the measured functional dependencies to one or more stored functional dependencies that correlate to a thermal aging curve to determine the heating cable's current location on the thermal aging curve.

DETAILED DESCRIPTION

Figure 1:
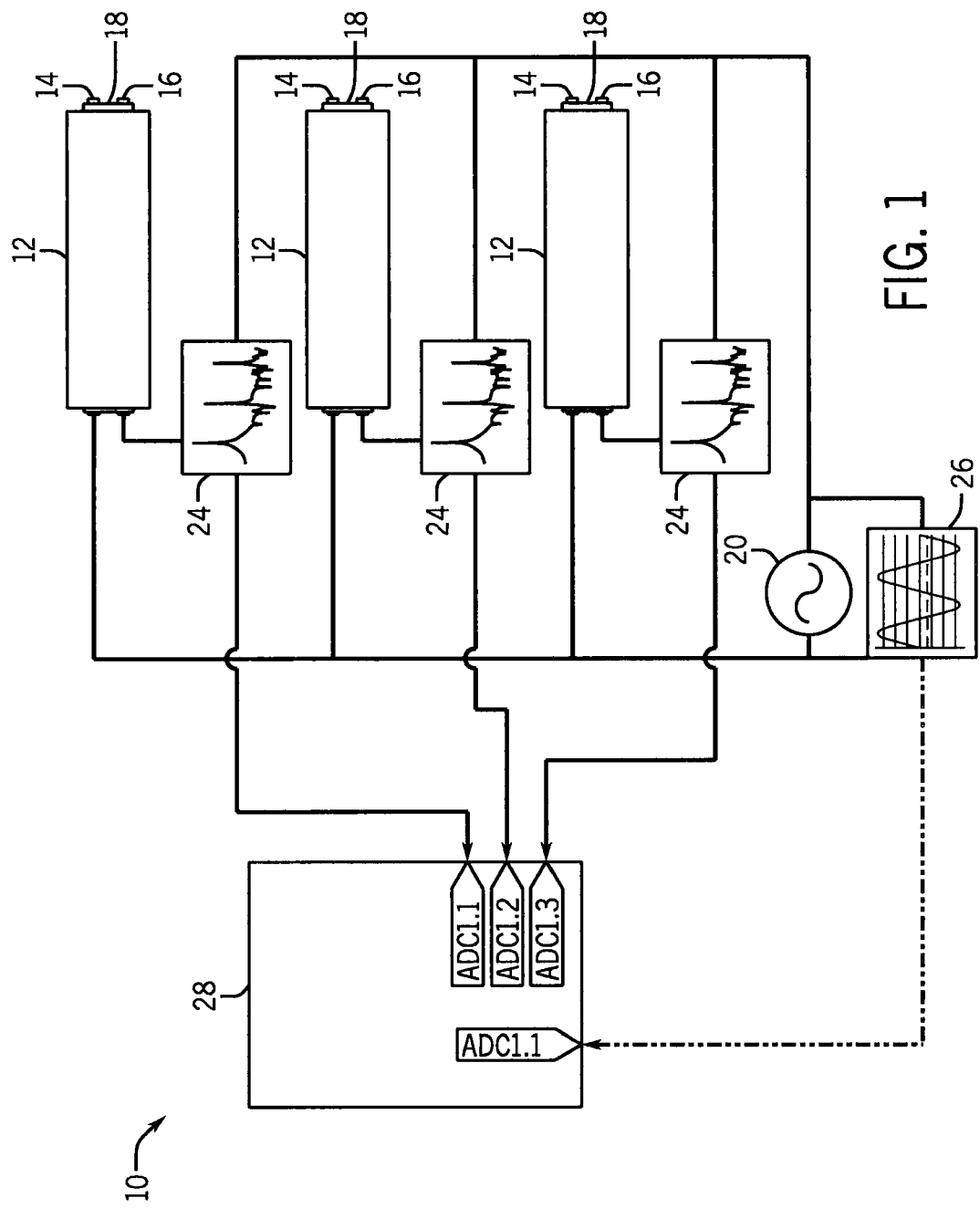
FIG. 1 is a schematic diagram of a system for tracking the thermal age of heating cables according to one embodiment of the invention.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives and fall within the scope of embodiments of the invention.

FIG. 1 illustrates a self-regulating heating cable thermal age tracking system 10 according to one embodiment of the invention. The system 10 can include monitoring and reporting arrangements for one or more circuits, each circuit including a heating cable 12. Suitable heating cables 12 include, without limitation, zone cables, self-regulating cables or other cables that have parallel bus wires 14, 16 for conducting current. In one implementation, the heating cable 12 is a solid-core self-regulating heating cable, having a semi-conductive polymer heating element 18 that substantially encases the bus wires 14, 16. The bus wires 14, 16 can be attached to opposite terminals of an alternating current power supply 20. The power supply 20 provides the electrical current, referred to herein as the line current, for all circuits. The line current may be produced at any suitable alternating current frequency, referred to herein as the line frequency. Typically, the line frequency is 50 Hz or 60 Hz, as provided by mains power, but the line frequency may deviate significantly from its expected frequency due to characteristics of components in the electrical system. With reference to the figures, the line frequency is described herein at 60 Hz, but it will be understood that the described systems and methods can be used with any line frequency or deviated line frequency.

A circuit monitor 24 can be disposed at a suitable position in the circuit for monitoring the cable signal as described below, such as between the second bus wire 16 and the power supply 20. The circuit monitor can contain current probes such as shunt resistors, Hall effect probes, induction coils or transformers, as well as subsequent conditioning electronics. An input voltage monitor 26 can be disposed in electrical communication with the power supply 20. The voltage monitor can be comprised of a sensing resistor or any other voltage meter and subsequent conditioning electronics. A control unit 28 can be configured to receive input from one or more of the circuit monitors 24 and the input voltage monitor 26. The control unit 28 can be a microcontroller, a digital signal processor, or another control device or array of control devices having suitable capacity for the desired system 10 implementation. The control unit 28 can be configured to extract the harmonic frequencies f of the base frequency: $f=n*f0$ ($f=120$ Hz, 180 Hz, 240 Hz, ... for $f0=60$ Hz) present in the line current. These harmonic constituents $A_n$, or the ratios between different harmonic constituents $A_{n1}/A_{n2}$, or any other functional dependence including two or more harmonics are monitored, recorded, transmitted to an analysis unit or indicated through a user interface. In one embodiment of the invention, the harmonic constituents or the ratios among different harmonic constituents are compared with an a priori measured correspondence curve or look-up table stored in the control unit 28, from which the present thermal age or remaining lifetime is calculated and indicated. In another embodiment of the invention, the analysis is done off-site after field service calls or regular transmissions of the harmonic constituents or ratios between different harmonic constituents from the control unit to a central location.

The system 10 can be configured to collect current and voltage measurements in the time-domain with an acquisition rate of at least 1 kHz. The system 10 can extract from the collected data spectral information regarding the frequency and amplitude of the line current supplied to the heating cable 12. The input voltage monitor 26 can collect line current data by being connected to the circuit across the power supply 20. This data stream is referred to herein as the "input signal" to the heating cable 12 and can contain one or more voltage measurements, as well as spectral information comprising frequency and amplitude components, for discrete time segments during which the data stream is collected. The input voltage monitor 26 can transmit the input signal to the control unit 28 for processing. The input signal can provide an independent measurement of the line frequency and its integer harmonics as well as their amplitudes to be used in extracting harmonic components from the cable signal. The circuit monitor 24 can collect a data stream for the line current as it is affected by the heating cable 12. This data stream is referred to herein as the "cable signal" and can contain one or more current measurements, as well as spectral information comprising frequency and amplitude components, for discrete time segments during which the data stream is collected. The circuit monitor 24 can transmit the cable signal to the control unit 28 for processing.

While the above circuits and the below methods are described with reference to self-regulating heating cables, the circuits and methods can be implemented for any self-regulating electrical system containing polymer-based, semi-conducting components which derive their conductivity from the addition of carbon black, carbon nanotubes or other conductive materials. Such self-regulating electrical systems are implemented according to the principles described with respect to the heating cable 12, and therefore can benefit from the described thermal age tracking methods.

Figure 2:
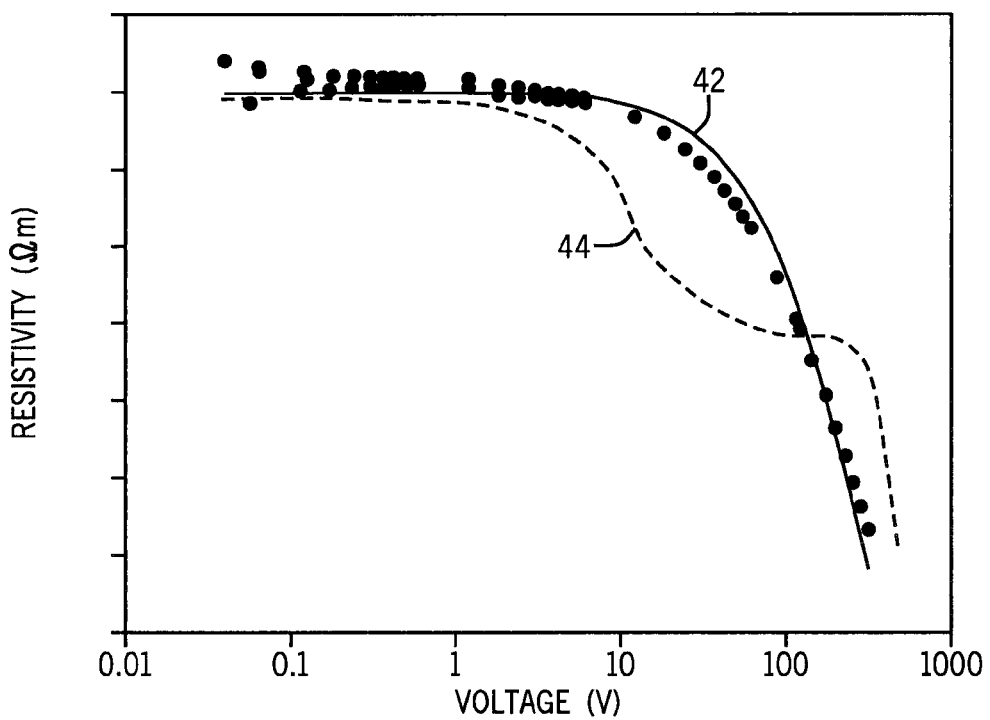
FIG. 2 is a graph of an example resistivity-versus-voltage curve of a self-regulating heater for an un-aged versus an aged sample cable.

The heating cable 12 is an intrinsically noisy environment that results in electrical losses due to the conversion, by design, of some of the line current into thermal energy. Additionally, the heating cable 12 has a nonlinear resistivity-versus-voltage relationship, which generates strong harmonic components of the line frequency relative to an Ohmic load. FIG. 2 illustrates a typical resistivity-versus-voltage curve 42 of an un-aged self-regulating heater versus the resistivity-versus-voltage curve 44 of an aged sample of the same type of self-regulating heater (dashed curve). If, as the cable 12 ages, the evolution of the harmonic components of the line frequency follows a different thermal age dependence from the line frequency itself, the relative contributions of the harmonics to the cable signal will change, yielding a potentially more universal (i.e., less dependent on the specific product sample) gauge of the thermal age than a measurement of the resistivity or power output. In particular, as demonstrated according to the algorithms described below, different odd harmonics of the line frequency degrade at different rates as the thermal age of the cable 12 increases, and the rates of degradation may be correlated with the thermal age of the cable 12.

Figure 3:
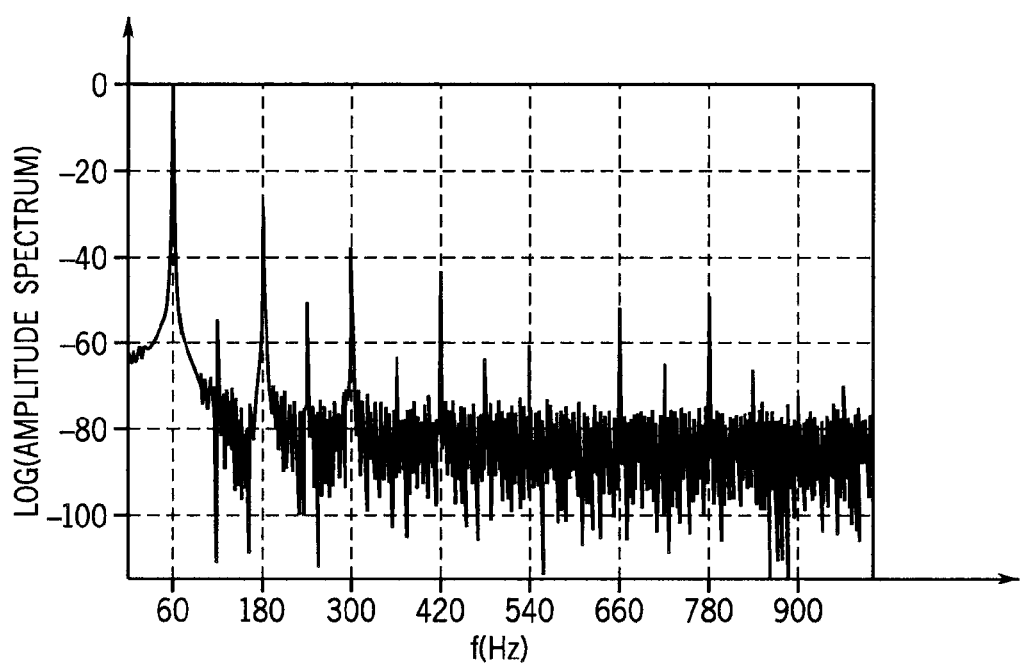
FIG. 3 is a diagram of an example current frequency spectrum for a heating cable.

FIG. 3 illustrates an example of the cable signal's spectral information when it is powered up under operating voltage conditions, at a point along a non-linear R(V) curve. A relatively flat baseline noise level is punctuated by amplitude peaks which, besides the dominant line current frequency, include odd harmonic components which are much stronger than in a standard load. As an illustration, in FIG. 3 the line frequency is about 60 Hz and the amplitudes of odd harmonics, 180 Hz and 300 Hz (and 420 Hz, and so on, in an increment of two times the line frequency), dominate. Enhancements on the even harmonics also exist, albeit on a much weaker scale, and not always visible above the noise level. The upper limiting frequency can be at least several times the line frequency, depending on the sampling rate and the integration window for the frequency extraction methods described below. The relative amplitude of the odd harmonics facilitates the extraction and analysis of the odd harmonic frequencies. The even harmonics, despite being less visible in the current spectrum, can be extracted using the same algorithm as is used for the odd harmonics.

The cable signal can be obtained directly from the heating cable 12, such as by collecting the data stream and deriving spectral information from the data stream as described herein in the field over the course of a baseline time scale, which may range from a few seconds to a few minutes. The baseline cable signal and all subsequent measurements for thermal age tracking are compared to a set of aging curves, look-up tables, or interpolated functions or routines obtained through laboratory testing of a representative sample of the heating cable 12, in advance of applying the tracking methods herein to the heating cable 12 in the field.

In some embodiments of the invention, the line current can be monitored, before and after passing through the heating cable 12, with a sampling frequency that is at least twice the maximum frequency to be analyzed, considering that a sampling frequency greater than the highest frequency of interest by an order of magnitude improves the quality of sampling. A sampling rate of 10 kHz is an adequate conservative value, but reasonable ranges are between 4-100 kHz. The time segments over which the collected spectral information is analyzed, and the harmonics or ratios between different harmonics are extracted, can be large enough to be statistically relevant, yet smaller than typical time scales over which the heating cable changes. For example, the time segments can be between a few seconds to hours, depending on the application.

The thermal age tracking methods described herein can be performed by a control unit or by any suitable computing unit or group of computing units. In some embodiments, some steps of the detection methods can be performed in the field, while others can be performed in a laboratory or other data analysis location remote from the location of the heating cable 12. For example, the spectral information can be collected by a data logger placed in communication with the heating cable 12, and the data logger can transmit the collected data through a wired or wireless connection to a central processing location. For ease of reference, the methods are herein described as being performed by a control unit, but it will be understood that other suitable data collection and processing architectures may be used. The thermal aging curve of the cable 12 is dependent on the composition of the cable 12; therefore, upon characterizing a cable 12 (e.g. RAYCHEM HWAT-R, T2Red, QTV, and LC2 heating cables, by Pentair Thermal Management), it is not necessary to obtain a sample of a deployed cable 12 of the same cable type to determine its age with the present methods. The curve(s) obtained through characterization provide the reference for determining the thermal age of the deployed cable 12 as described below.

Figure 4:
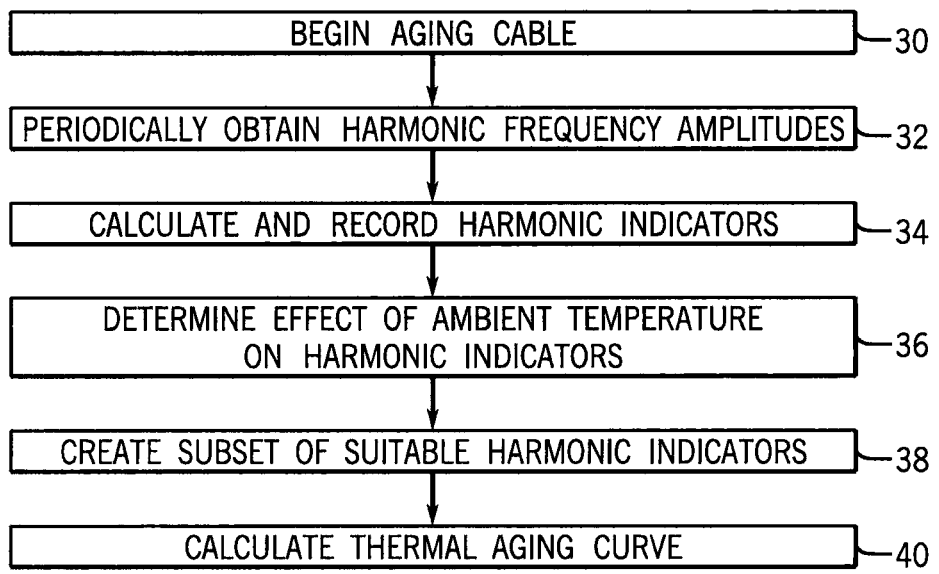
FIG. 4 is a flowchart showing a method of determining the harmonic signatures or indicators as a function of the thermal age of a self-regulating heating cable.

FIG. 4 illustrates an exemplary method for characterizing a cable 12. At step 30, an artificial aging process is initiated upon a new (i.e. previously unused) length of cable 12. The length may be any length suitable for testing because the thermal age characteristics of a cable 12 are not dependent on its length. During this testing, the temperature must be well-defined and kept constant throughout the length of the aged sample. Artificially aging the cable 12 includes heating the cable 12 to a predetermined stressing temperature and maintaining the cable 12 at or within about 0.5 degrees Celsius of that temperature for a desired aging duration. Heating may be performed in an industrial oven or other suitable heating device. The stressing temperature is selected to accelerate the thermal degradation of the cable 12 to a suitable testing duration. As with the cable 12 length, the value of the stressing temperature does not impact the accuracy of the spectral information for representing the actual thermal age of the cable 12, as long as the aging is still described by the Arrhenius law equation above. That is, the cable 12 ages on a curve that is a function of the power output of the cable 12, which is dependent upon the polymer and other materials that comprise the cable 12. However, stressing temperatures too close to the polymer melting temperatures do not result in repeatable and well-defined relationships between the harmonics and the thermal age any longer, and should be avoided. The curve data can be obtained at any temperature high enough for reasonably fast aging, but far below the melting temperature of the polymer, and the thermal age can be extracted from the curve at any temperature as described below. Following the Arrhenius law, the same thermal age can be obtained through any number of trajectories in the temperature—exposure time phase space, and a given thermal age can correspond to either longer exposure at lower temperature or shorter exposure at higher temperature: $B*time1*exp(-C/T1)=B*time2*exp(-C/T2)$.

In contrast to limiting the stressing temperatures to far below the melting point of the cable 12 polymer, if a cable installed in the field is subjected to such high temperatures, the present systems will tend to interpret the associated signal as representing an uncharacteristically highly-aged cable 12. Such high temperatures can be beyond the recommended safe operating specifications, so the highly-aged interpretation is a desirable effect because it can be used to provide a warning for unsafe operating conditions. In particular, the present systems can compare the calculated thermal age to the actual deployment duration of the cable 12, to the thermal ages of contemporaneously installed similar thermal cables, or to another indicator of relatively acceptable thermal aging of the cable 12. The system can produce an alert or take another preventative or protective action if the cable 12 thermal age is above a certain threshold.

The aging duration may be a predetermined number of days at a predetermined characteristic temperature, or may be a variable duration that continues until the tested power output of the cable 12 decreases to a threshold "dead" output at which the cable 12 would need to be replaced if it were deployed.

At step 32, while the cable 12 is aging, periodically the amplitudes of harmonics of the line frequency of the cable signal are obtained by electrical measurement of the cable signal and extraction of the harmonic frequency components therefrom. Each point of periodic collection constitutes a data point on the thermal aging curve. In some embodiments, the cable signal can be collected while the cable 12 is aging in the heating device. In other embodiments, the cable 12 is removed from the heating device and transferred to another temperature-regulating device, such as a circulator or heat bath, so that the cable signal can be collected at several temperatures. The cable 12 can be attached to a cable signal monitoring circuit, such as that described above with reference to FIG. 1, and the line current through the cable 12 can be sampled to obtain the cable signal. A line frequency signature, present in the spectral information of the cable signal, can be extracted from the cable signal. The line frequency signature includes the base line frequency (typically 50 or 60 Hz) and its harmonic frequencies up to the highest frequency of interest, typically between 0.5 and 1 kHz. The amplitudes of the desired harmonics are then obtained from the line frequency signature.

One or more of the harmonic components of the line frequency signature may be dependent upon the ambient temperature of the cable 12 at the time the line current is sampled. The line current can be sampled while the ambient temperature of the cable 12 is held at one or more discrete temperatures. The discrete temperatures can include a range of temperatures typically lower than the stressing temperature, where the range can, but does not need to, include temperatures separated by a common interval. Obtaining the harmonic aging curves at different temperatures can be used to eliminate the ambient temperature effect from the interpretation of the data, by obtaining a plurality of independent harmonic measurements with different ambient temperature dependences. The cable signal data can be stored for later line frequency and harmonic signature extraction, or the line frequency signature and/or harmonic components can be extracted and stored, and the unneeded spectral information from the cable signal discarded.

It might be necessary to eliminate the effect of the ambient temperature by utilizing the different ambient temperature dependencies of different harmonic coefficients, and at the same time extract the thermal age, whereas the ambient temperature can play a less significant role or, in yet other situations, can be relatively easily determined. FIGS. 6, 7A-B, and 8A-B illustrate the simultaneous extraction of both ambient temperature and thermal age, whereas the actual methodology can be a more complex algorithm, including but not limited to a look-up table or extrapolated functional dependencies. See details on the extraction of both ambient temperature and thermal age below.

The thermal age can be reported to a user as the remaining heater power output left, as the remaining lifetime based on an expected standard deployment temperature until the power output will drop to a certain threshold, or a higher-level interpreted user interface signal such as a recommendation to exchange the installed heating cable within a certain time frame.

Figure 5:
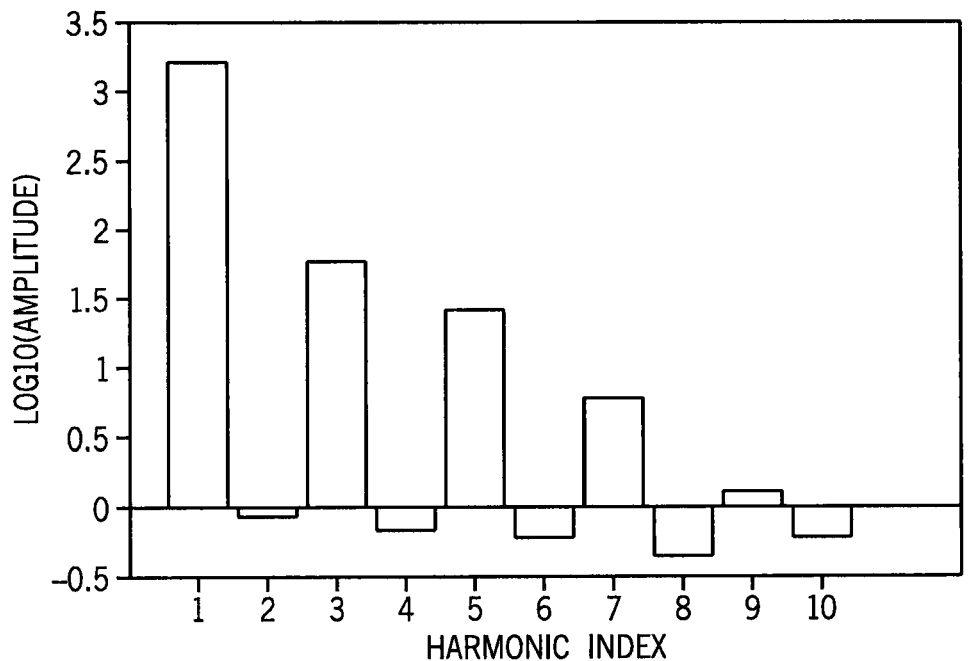
FIG. 5 is a bar graph of amplitudes of ten harmonic components of the cable signal of a self-regulating heating cable attached to mains power.

FIG. 5 shows the extracted harmonic amplitudes for the line frequency and the first nine harmonic modes (e.g. bar 1 is 60 Hz, bar 2 is 120 Hz, bar 3 is 180 Hz, and so on) on a logarithmic mA-scale for an example cable 12 fully powered up using 208V line power. As expected, the odd harmonics ($f=(2N+1)f_0$, $N=0, 1, \ldots$) dominate and represent a consistent and accurately measureable signal up to at least the $9^{th}$ or $11^{th}$ harmonic. In FIG. 5, the amplitude of the two first major harmonics is 2-4% of the fundamental, which can be larger or smaller in different types of self-regulating heaters, but always measureable by current sensing probes in standard controllers. Hence, the odd harmonics will be the primary signal to be measured and analyzed.

Even harmonics are much smaller and therefore much more sensitive to noisy line power. However, even harmonics, the ratios between odd and even harmonics and ratios between different even harmonics can be an indicator of thermal age just as odd harmonics or the ratios between different odd harmonics. Even harmonics are extracted during the same signal processing and analysis stages as odd harmonics, and any analysis with respect to thermal aging curves will follow the same or similar algorithms At step 34, for each data point at which the harmonic amplitudes are obtained, one or more harmonic indicators are calculated and recorded. A harmonic indicator is a measurement derived from information in the harmonic frequency components of the line signal that can be used to determine the thermal age of the cable 12. The harmonic indicator may be the amplitude of one or more of the harmonics, as well as a calculated function of a plurality of harmonics, such as a ratio of two harmonic component amplitude peaks, or a function of more than two harmonic component amplitude peaks. Any two harmonics may be components of each calculated ratio. In some embodiments, adjacent odd harmonics (i.e. first (line frequency) and third harmonics, third and fifth, fifth and seventh, and so on) comprise each ratio. One or more ratios for each pair of harmonic components may be calculated from the stored amplitude data according to any suitable data compilation. In one non-limiting example of such data compilation, the amplitude peak for each desired harmonic is measured for each discrete ambient temperature at a plurality of time samples, and the amplitude peaks for each ratio can be averaged across the time samples.

Figure 6:
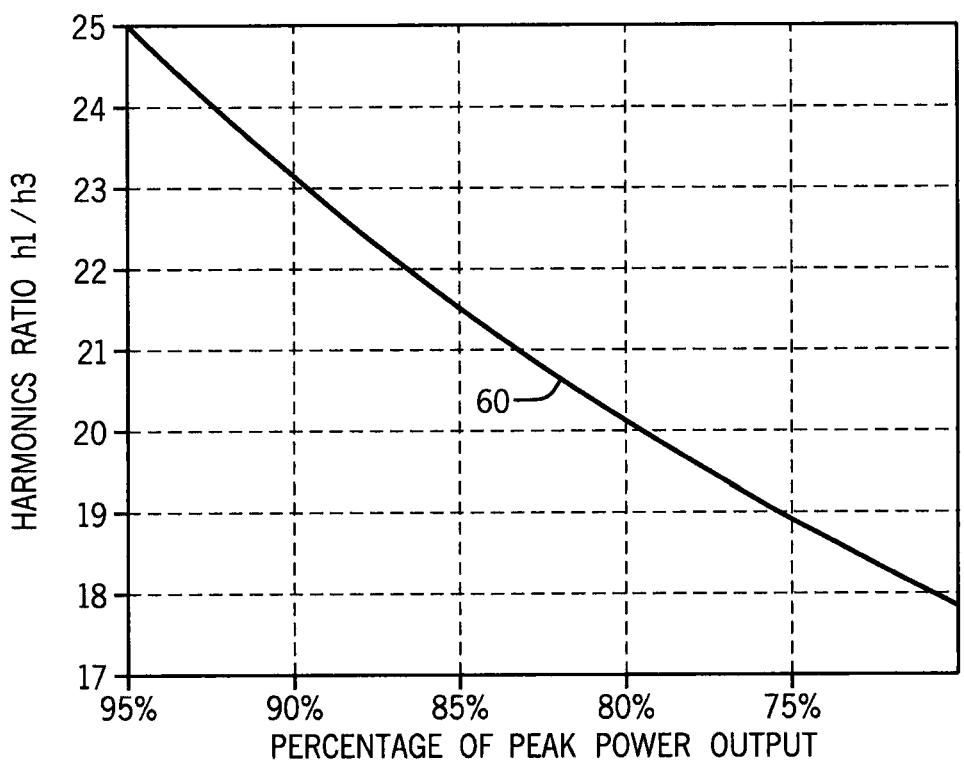
FIG. 6 is a graph of a single calibration curve for the value of a harmonic ratio with weak dependency on ambient temperature, plotted against the percentage of peak power output of a cable.
Figure 7A:
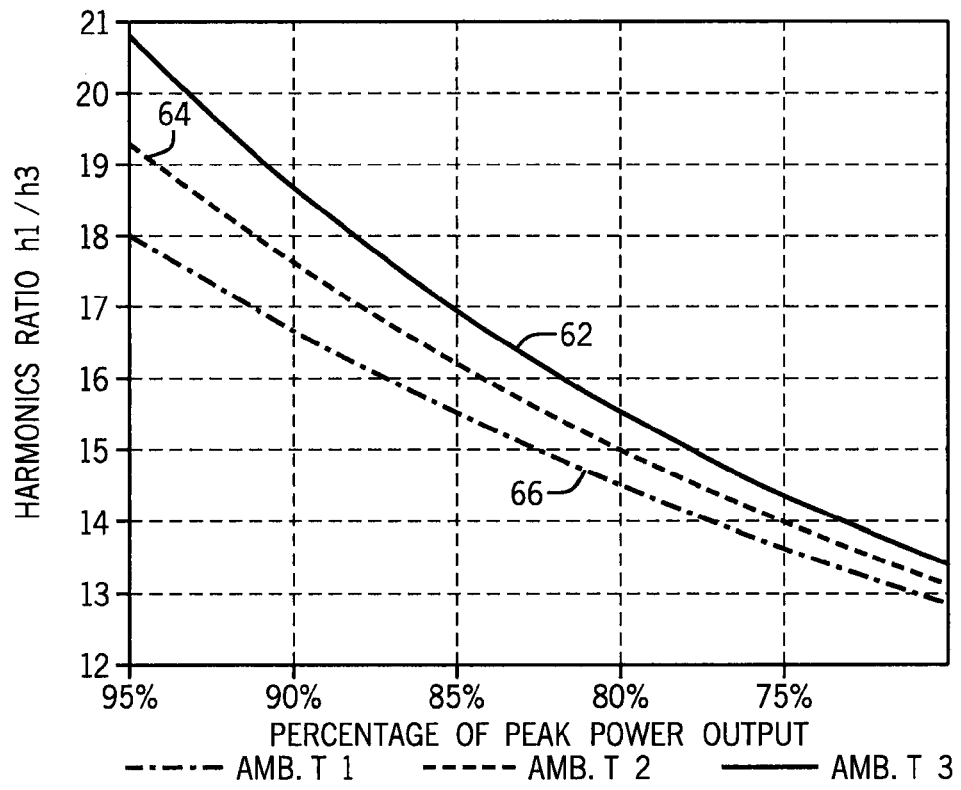
FIG. 7A is a graph of three temperature-dependent calibration curves for the values of a single harmonic ratio in an example cable type, plotted against the percentage of peak power output of the cable.
Figure 7B:
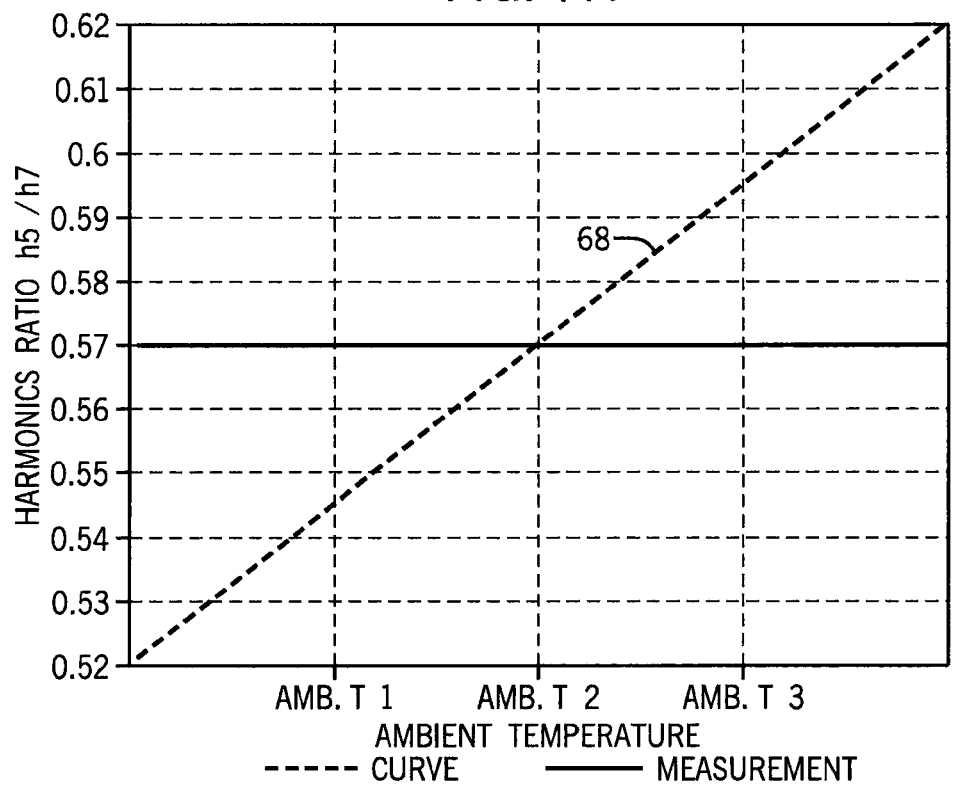
FIG. 7B is a graph of a harmonic ratio value at different ambient temperatures.
Figure 8A:
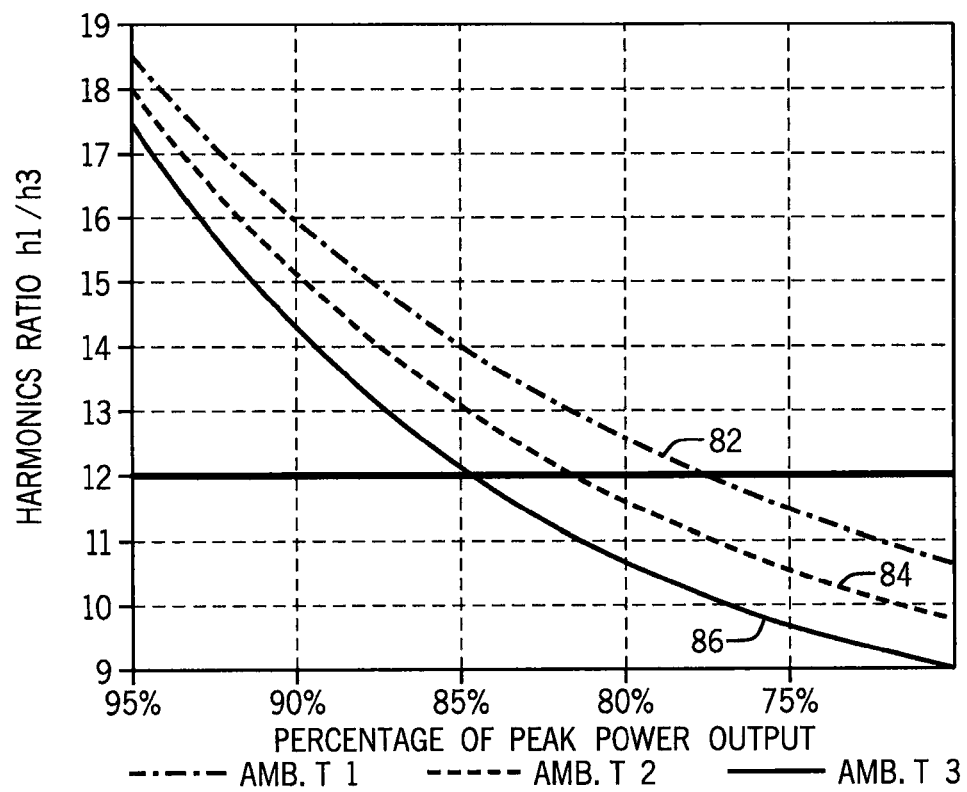
FIG. 8A is a graph of the calibration curves for a first harmonic ratio in an example cable, each calibration curve representing the first harmonic ratio values at a certain ambient temperature.
Figure 8B:
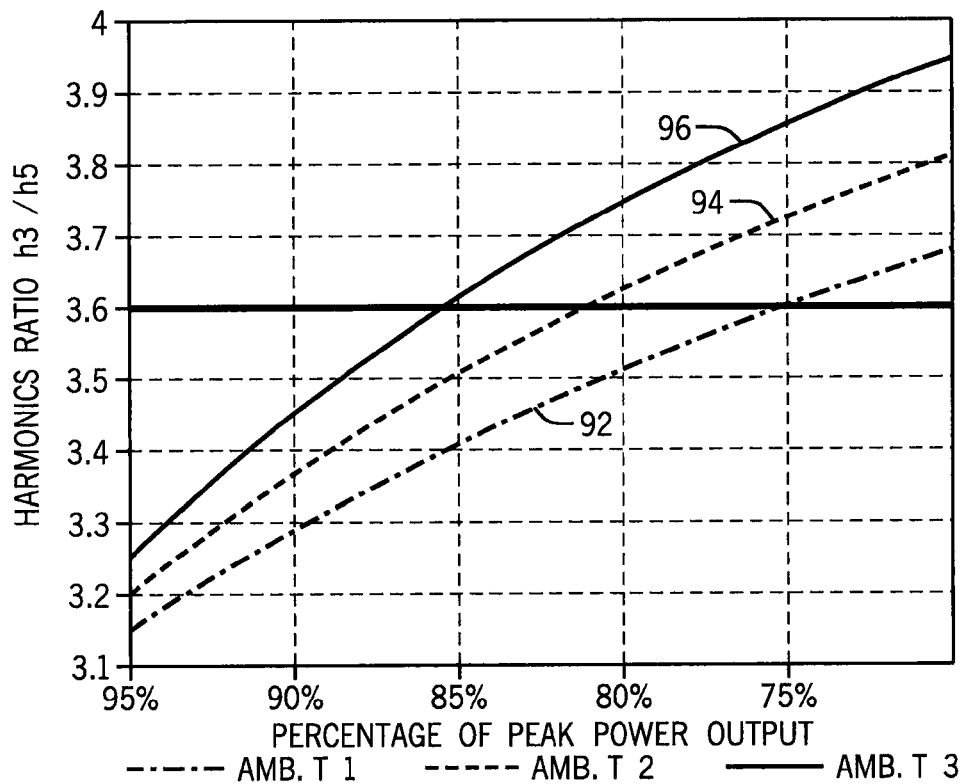
FIG. 8B is a graph of the calibration curves for a second harmonic ratio in the example cable of FIG. 8A, at the ambient temperatures of the graph of FIG. 8A.

FIGS. 6, 7A-B, and 8A-B illustrate representative curves for ratios between different harmonics versus thermal age in particular demonstrative cases. In FIG. 6, the ambient temperature has a negligible influence to the application. In FIGS. 7A-B, the ambient temperatures can be easily determined using a harmonic indicator which is dependent on ambient temperature, but independent on thermal age. FIGS. 8A-B illustrate the most general case for two independent harmonics ratios with different dependencies on ambient temperature. The following description is similar for any other harmonics ratios other than the ones shown, and also if instead of harmonic ratios, the harmonics themselves or any other functional dependence between two or more harmonics, are used, as long as two or more different harmonic indices contribute to the analysis.

As shown in FIG. 6, a first calibration curve 60 represents the ratio of the first harmonic (i.e. the line frequency) to the third harmonic. For the illustrated cable 12, the first-to-third ratio decreases as the power output of the cable 12 decreases (i.e., as the cable 12 ages), indicating that the first harmonic amplitude degrades faster than that of the third harmonic. The slope, trend, and other components of the calibration curves for the various ratios in different types of heater cables may differ. When the ambient temperature at deployment is similar to the ambient temperature at which the harmonic aging curves were acquired in the lab, or if the influence of the ambient temperature on the calibration curves is negligible, this ratio may be directly correlated to the thermal age of the cable 12. Therefore, referring again to FIG. 4, at step 38 a subset of suitable aging ratios may be created, and the subset may include the first-to-third harmonic ratio at each data point. From this subset, at step 40 a thermal aging curve for the cable 12 may be calculated, whereby a particular first-to-third harmonic ratio correlates to a thermal age of the cable 12.

In most cables 12, especially at more widely varying deployment temperatures, a ratio of a single pair of harmonics or another single harmonic indicator may be insufficient to completely characterize the cable 12 because one or more of the harmonics may be sensitive to ambient temperature. For example, as shown in FIG. 7A, either or both of the first and third harmonics of the example cable 12 reach a different amplitude at different ambient temperatures, so that the first-to-third harmonic ratio depends on the ambient temperature. The resulting temperature-sensitive calibration curves 62, 64, 66 for this ratio show that it alone cannot track the thermal age of a deployed example cable 12 because the ambient temperature at the time the cable signal for the deployed cable 12 is collected may be unknown. To account for temperature susceptibility, the ambient temperature can be measured through an independent sensor or sensors distributed along the heater. However, this requires additional sensors within the system. Instead, harmonic comparison methods may be used by the present system, wherein a ratio of at least one additional pair of harmonic components (or a second other harmonic indicator) is needed to either determine the ambient temperature at the time of measurement, or to eliminate the uncertainty caused by temperature fluctuation through correlative comparisons of the ratios. Thus, referring again to FIG. 4, at step 36 the effect of ambient temperature on a plurality of harmonic indicators (e.g., ratios) can be determined before creating the subset of indicators in step 38.

In some embodiments, where the first ratio is susceptible to both aging and temperature, the second ratio can be one that is independent of or only weakly dependent on aging, but strongly dependent on temperature. In some types of cables, for example, the relative difference in amplitudes between the fifth and seventh harmonics remains substantially constant as the cable 12 ages, and the fifth-to-seventh harmonic ratio in the example cable 12 will show little change in the thermal aging curve (i.e., the value of $A_5/A_7$ remains substantially constant as percentage of peak power output decreases). However, as shown by temperature curve 68 in FIG. 7B, the fifth-to-seventh harmonic ratio can have a significantly different value depending on the ambient temperature. Because the age of the cable 12 has an insignificant impact on the ratio, the ratio can be used to determine the ambient temperature at the time of measurement. That is, the value of the ratio (e.g., 0.57 as indicated by the example bold black line) correlates to a particular ambient temperature (e.g., Amb. T2) on the graph of FIG. 7B. The ambient temperature can then be eliminated as a variable in interpreting the first-to-third harmonic ratio from the chart of FIG. 7A, without separately sensing the temperature, so that the thermal age can be determined from that ratio. Thus, in these embodiments, the subset of suitable ratios created at step 36 can include the first-to-third harmonic ratios at a plurality of discrete temperatures at each data point, and the fifth-to-seventh harmonic ratios at a plurality of discrete temperatures at least at one data point. If uncertainty remains after incorporating the second ratio, additional ratios (e.g. the seventh-to-ninth or ninth-to-eleventh harmonic ratios) may be calculated and included in the subset. The correlative thermal aging curve created at step 40 would then include the additional ratios as references linking the first ratio's values to points on the curve.

In other embodiments, different harmonics ratios increase or decrease with both the thermal age and the ambient temperature, so that one or more general optimization algorithms (e.g. linear interpolation or cubic spline fit in the two-dimensional parameter space of ambient temperature and deployment time, as non-limiting examples) are required to find the thermal age and ambient temperature which best explains all observed harmonic ratios. An example algorithm sequence is outlined as follows, with references to FIGS. 8A and 8B which, respectively, show calibration curves 82, 84, 86 for $A_1/A_3$ (the ratio between the first and third harmonics) and associated calibration curves 92, 94, 96 for $A_3/A_5$ (the ratio between the third and fifth harmonics) of the same cable 12 versus thermal age and for the same three ambient temperatures T1, T2, T3:

Taking measurements at a given point in time, e.g., h1/h3=12 (solid horizontal line in FIG. 8A) and h3/h5=3.6 (solid horizontal line in FIG. 8B) fully determines both ambient temperature and thermal age.

From the stored calibration curves of harmonic ratios versus thermal age and ambient temperature, the measurements can be used to extract functional relationships, such as functional dependencies, of the permissible thermal age versus ambient temperature. One such relationship THERMAL AGE (AMBIENT TEMPERATURE) is determined from each FIG. 8A and FIG. 8B. For that extraction, interpolation schemes such as linear interpolation of cubic spline interpolation can be used.

From the two relationships of THERMAL AGE (AMBIENT TEMPERATURE) extracted from FIG. 8A and FIG. 8B, a unique value for both thermal age and temperature can be, for example, determined through a steepest-decent, iterative optimization algorithm, which minimizes the difference in the thermal age for both curves 8A and 8B, and determines the ambient temperature at which they are minimized, which in turn gives us the thermal age.

Figure 9:
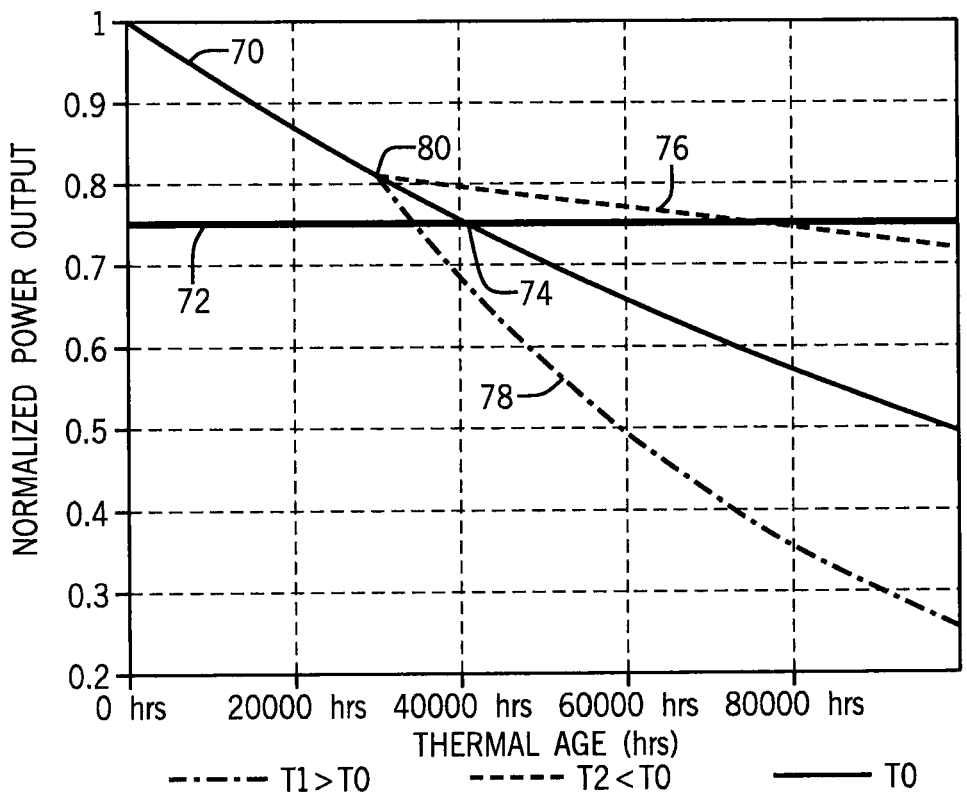
FIG. 9 is a line graph of a thermal aging curve with a predictive component.

Referring to FIG. 9, the thermal aging curve 70 thus correlates the relevant subset of ratios to the thermal age of the cable 12. The Y-axis is the power output of the cable 12 as a percentage of the original rated output. The X-axis is the thermal age, measured in the number of hours of exposure to a nominal temperature, where hours spent above or below the nominal temperature count proportionally toward the total, and thus increase or decrease the rate of thermal aging. The curve 70 intersects a minimum power output 72, typically about 75% of the original rated output. This intersection 74 therefore represents a "dead" cable 12. Each of the selected ratios correlates to a discrete thermal age, and thus to a point on the curve 70.

Once the cable 12 has been characterized, characterization data including the thermal aging curve 70 and stored ratio calculations can be provided to the control unit that monitors a deployed cable 12. In particular, the control unit can store or access the thermal aging curve 70, and can further store or access a list or other record describing the ratios that are included in the subset created at step 38. The control unit can be configured to collect the cable signal, such as in a monitoring circuit, and perform the harmonic component amplitude extraction and the ratio calculation. The control unit may calculate only the relevant ratios if it has knowledge of which ratios were used to create the thermal aging curve 70. Alternatively, the control unit may calculate some or all of the harmonic ratios up to a suitable harmonic order. The control unit determines, from the measured and calculated ratios and the thermal aging curve 70, the present thermal age of the cable 12 by comparing the measured ratios to the stored ratios. The control unit can perform these data collection, extraction, calculation, and comparison steps continuously, at a predetermined interval, or upon request by a human or computer controller.

The control unit can further provide predictive data to a user. The predictive data can include an estimation of the remaining useful life of the cable 12 based on the measured ratios and the cable's 12 current location 80 on the curve 70. The control unit can implement one or more approaches to estimating the remaining life of the cable 12. In one embodiment, the control unit can subtract the number of hours represented by the cable's 12 current location 80 from the maximum rated life span of the cable 12 to produce the estimated number of hours remaining. However, this method does not take into account that the cable 12 may historically have been aging faster or slower than typical rate, for example due to different ambient temperatures. In another embodiment, the control unit may have access to the actual age of the cable 12. The actual age is the number of hours the cable 12 has been deployed. The control unit may retrieve the actual number of hours, or may retrieve the installation date of the cable 12 and calculate the actual age from that date. From the actual age, the control unit can determine if the cable 12 is aging faster or slower than normal, and at what proportional rate. From the proportional rate and the rated lifetime of the cable 12, the control unit can estimate the remaining useful life curve and its intersection with the minimum power output 72. Additionally, from this data the control unit can determine the average temperature at which the cable 12 has been operated over its life, and can provide this information to the user. The control unit can further provide alternative useful life scenarios, such as a power-saving curve 76 estimating a longer life if the average temperature of the cable 12 can be reduced, and an extreme-use curve 78 estimating a shorter life if the average temperature of the cable 12 increases. In another embodiment, the control unit can estimate remaining useful life based on user input. For example, the user can access the control unit via an interface and provide one or more projected average operating temperatures over the cable's 12 remaining life. Based on the calculated current position 80 and the inputted temperature(s), the control unit can provide one or more scenario curves 76, 78 to the user. In other embodiments, higher level indicator signals or alerts derived from the above data can recommend that the cable be exchanged or serviced within a certain time frame.

Figure 10:
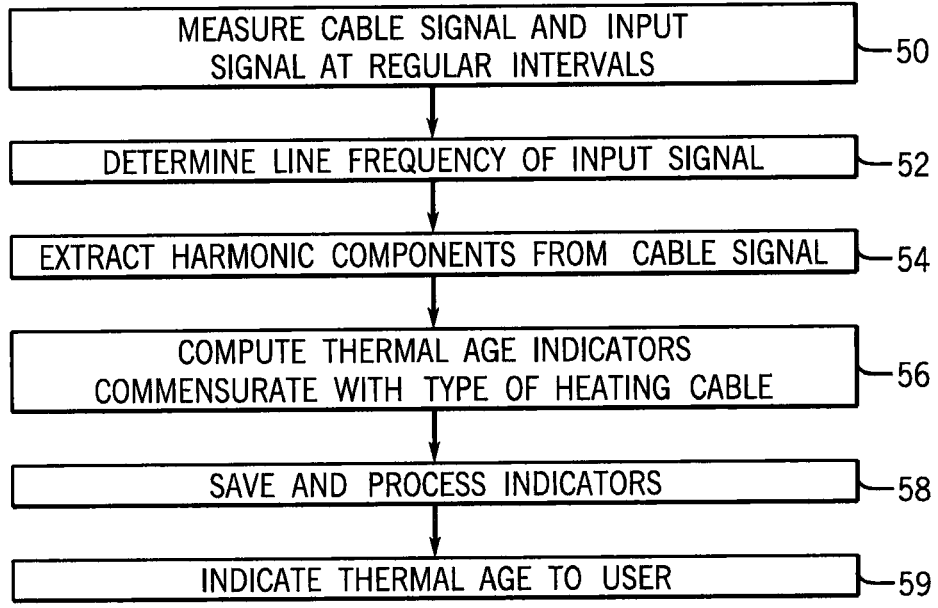
FIG. 10 is a flowchart of an exemplary method of extracting a deployed cable's thermal age from electrical measurements of cable and input signals.

FIG. 10 illustrates an exemplary method for periodically extracting the thermal age, remaining power output and life expectancy of a deployed cable 12. At step 50, the input signal can be obtained from the power supply 20 or from the heating cable 12 and the cable signal can be obtained from the heating cable 12. The input signal includes frequency and amplitude components of the line current. The line frequency is either 50 Hz or 60 Hz depending on jurisdiction, but fluctuations in the current may continuously shift the line frequency by up to 5 Hz or more away from the theoretical frequency, particularly if the power supply is from a local source such as a generator. In order to accurately identify and extract the harmonic components, at step 52, the control unit can determine the actual, real-time line frequency. Then, at step 54, the control unit can extract the actual line frequency and its harmonics. The control unit can use any suitable spectral analysis and frequency extraction method, including without limitation: an adaptive tracking algorithm, which extracts the dominant frequency of the line voltage and the harmonic components of the heater current through iterative optimization steps; a frequency-domain method such as a discrete Fourier transform (DFT), where the peak fundamental frequency and harmonic coefficients are extracted; or, a Goertzel transform to extract individual frequency components from the data stream, which can be more efficient than a DFT if only a few harmonic frequencies need to be extracted. Both odd harmonic frequencies ($f=(2N+1)f_0$, $N=0, 1, \ldots$) and even harmonic frequencies ($f=2Nf_0$, $N=0, 1, \ldots$) can be extracted.

A special adaptive tracker can be designed for this application which advantageously meets the following four criteria: representation as an infinite impulse response (IIR) filter with a small number of coefficients ($n \ll 10$); reaction time in case of line fluctuations within a few line cycles $N \cdot (1/60 \text{ Hz})$, which is equivalent to <1000 samples at a sample rate of 10 kHz; capability to track all harmonic components at the same time; and, avoidance of "overfitting", i.e., fitting noise with adaptive fit to harmonic terms.

Adaptive tracking algorithms tend to converge faster if fewer harmonic frequencies are present. An adaptive tracking filter implemented in one embodiment therefore can use a hybrid approach: first applying a stable, fast-converging filter to the input signal which has weak higher harmonic components to determine the line frequency, then applying the line frequency thus gained to the cable signal to extract the fundamental and harmonic amplitudes.

The tracking filter to determine the fundamental frequency implemented in one embodiment applies a filtering algorithm that matches the input voltage signal function $V(t)$ to the harmonic functions $y(t)$, $\phi(t)$:

$$\phi(t) = \omega(t)t + \delta(t)$$

$$y(t) = A(t)\sin(\phi(t))$$

by minimizing the differential $e(t)$ between the input signal function $V(t)$ and the function $y(t)$:

$$e(t) = |V(t) - y(t)|$$

The control unit can recalculate and minimize $e(t)$ continuously or at regular intervals in order to track the line frequency $\omega$, amplitude $A$ and phase $\phi$. The minimization of the residual $e(t)$ can be performed by gradient descent or any other optimization method known to those skilled in the art.

As a consequence of the determination of the base frequency, subsequent harmonics are also extracted from the signal by minimizing the residual $e_n(t)$ for each harmonic term n.

In the cable signal, the Ohmic (fundamental) current will follow the same frequency behavior as the line voltage, whereas the same phase is not enforced or assumed. A priori, the distribution of the current on the different harmonics is not known and needs to be determined. With the known fundamental frequency from the input signal, the higher harmonics ($f=Nf_0$, $N>1$) can be determined simultaneously by formulating the problem as another optimization problem, with the difference that the frequencies are a prior known this time.

The following iterative sequence is conducted at each measurement point t in time, whereas an arbitrary starting assumption on the harmonic contributions at different frequencies $I_n$ needs to be made. Starting from the first harmonic, and iterating through all higher harmonics until the maximum iteration of interest (typically 10-20), the amplitude contribution of each harmonic current mode $I_n$ is found by computing the deviation $e_f(t)$ between the total measured current $I_{meas}(t)$ and the sum of all harmonic contributions up to the present iteration m:

$$e_m(t) = I_{meas}(t) - \sum_{n=0}^{m} \dot{I}_n(t) * f_{meas}$$

Based on these computed residuals, the harmonic contributions to the cable current are updated after each time step in such a way that the residuals $e_m(t)$ are minimized. In line with the physics of self-regulating heating cables, the different harmonics are assumed to be in phase with each other, so that the current (amplitude) contributions are the only unknowns.

In one embodiment of the invention, the harmonic current contributions are updated by integrating a second-order differential equation $\ddot{I}_n(t)$ which utilizes the functional form of a sine or cosine function for each harmonic contribution. This is numerically equivalent to a filter with two recursive IIR-coefficients. Using the latter, the computational efficiency requirement of the filter is well satisfied. Even in the worst-case scenario, the optimization has reached a steady state, marking the solution of the optimization problem, within less than a few power line cycles, even for a large number of harmonics extracted.

The adaptive filter was subjected to intensive testing. A sudden change in the fundamental frequency by 0.2 Hz or greater is matched to within 5 fundamental periods (for regular power grid operation, the rates of change of line frequency are typically much less than 0.01 Hz per cycle). As expected, sudden changes in amplitude are matched even faster, as are additional harmonic components which suddenly appear.

In one embodiment, the control unit has a set of harmonic curves versus thermal age and ambient temperature for the deployed type of cable stored and uses appropriate data analysis techniques to extract the thermal age, while eliminating the effect of ambient temperature. In another embodiment, the control unit transmits the data to an external nearby or remote location, where it is analyzed. In yet another embodiment, the data are collected during a field service intervention using a data logger or other measurement device and analyzed in a remote location. In any embodiment, the method can include, at step 56, computing the indicators to be used for generating the harmonic curves. The selected indicators to be computed may have been determined during calibration, and therefore may be specific to the heating cable 12 type. At step 58, the computed indicators are processed according to one of the embodiments described above (e.g., the control unit may determine the thermal age in situ, or may transmit the computed indicators to a remote processor). At step 59, the thermal age may be reported to the user. Such reporting may include an alert that the cable 12 is reaching or has reached the end of its expected useful life.

As described herein, the relationships among different harmonics, such as even versus odd, or among different odd harmonics, are a gauge of the thermal aging of the heating cable 12 and can be used to help a system owner or engineer plan the replacement schedule for heating cables. The following properties, among others, of the harmonic signatures render harmonic monitoring a superior thermal age indicator compared to only resistivity measurements:

It provides the first true in-situ measurement of the thermal age or remaining power output of a heater, since only measuring the power consumption of the heater does not provide sufficient information, because the output depends on the temperature distribution along the heater, which is not accurately known.

the relative weight of odd current harmonics is stable with respect to power-up/inrush versus power equilibrium, i.e., there is a gauge for thermal aging largely independent of the operating state of the heating cable;

the harmonic content in the heater current can be consistent within cables 12 of the same product type, rendering the thermal age measurement independent of any baseline measurement for a particular cable 12;

the distribution of different harmonics in the heater current is independent on its overall resistivity and, therefore, length, so modifications to the deployed cable 12 such as cutting or splicing would not falsify the thermal age measurement;

due to the large number of available harmonics, there are multiple derived measurements which can be conducted, as opposed to one single measurement in the case of resistivity; and the described tracking methods are robust and computationally inexpensive enough to be deployed as an add-on to existing controllers, or deployed in a low-cost extra circuit.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein. Various features and advantages of the invention are set forth in the following claims.

The invention claimed is:

1. A method of determining a thermal age of a heating cable in an electrical system, the electrical system including a control unit that monitors the heating cable, the method comprising:
   receiving, by the control unit, a thermal aging curve associated with a type of the heating cable, the thermal aging curve being generated by:
      applying a thermal aging process to an example cable having the type;
      at discrete data points in time during the thermal aging process, collecting from the example cable a test cable signal generated by passing a current through the example cable;
      extracting, from the test cable signal collected at each data point, a plurality of amplitude components each representing a corresponding amplitude of one of a plurality of harmonic frequencies of the line frequency;
      for each data point, calculating one or more ratios of one or more pairs of the amplitude components;
      storing at least one of the ratios corresponding to each data point; and
      correlating each of the stored ratios with a corresponding location of a plurality of locations defining the thermal aging curve;
   receiving, by the control unit, a cable signal generated by passing a line current through the heating cable;
   extracting, from the cable signal by the control unit, spectral information comprising a line frequency, one or more harmonic frequencies of the line frequency, and an amplitude component for each of the line frequency and harmonic frequencies;
   calculating, by the control unit, one or more measured functional dependencies between one or more pairs of the harmonic frequency amplitudes; and
   comparing, by the control unit, each of the measured functional dependencies to one or more of the stored ratios to determine a current location of the heating cable on the thermal aging curve, the current location indicating the thermal age of the heating cable.

2. The method of claim 1 wherein extracting the spectral information from the cable signal comprises:
   determining the line frequency from the line current before it passes through the heating cable; and
   applying an adaptive tracking filter to the cable signal, the adaptive tracking filter being configured to use the line frequency to obtain the harmonic frequencies.

3. The method of claim 1 wherein the one or more harmonic frequencies correspond to odd harmonics of the line frequency.

4. The method of claim 3 wherein each pair of harmonic frequency amplitudes corresponds to adjacent odd harmonics.

5. The method of claim 1 wherein the measured functional dependencies comprise a plurality of measured ratios, and wherein comparing the measured functional dependencies to the stored ratios comprises:
   comparing a first of the measured ratios to one or more of the stored ratios to determine a temperature of the heating cable at the time the cable signal was collected;
   selecting a second of the measured ratios that corresponds to the determined temperature; and
   comparing the second measured ratio to one or more of the stored ratios to determine the current location of the heating cable on the thermal aging curve.

6. The method of claim 5 wherein comparing the measured functional dependencies to the stored ratios further comprises selecting one or more third measured ratios and comparing the one or more third measured ratios to one or more of the stored ratios.

7. The method of claim 1, further comprising obtaining, by the control unit from a temperature sensor in communication with the control unit, the temperature of the heating cable at the time the cable signal was collected, wherein comparing one or more of the measured functional dependencies to the one or more stored ratios comprises selecting a first of the measured functional dependencies that corresponds to the obtained temperature and comparing the first measured functional dependence to one or more of the stored ratios to determine the heating cable's current location on the thermal aging curve.

8. The method of claim 1 further comprising predicting, by the control unit based on the thermal aging curve and the current location on the thermal aging curve, a remaining useful life of the heating cable.

9. The method of claim 8, further comprising:
   receiving, by the control unit via an interface in communication with the control unit, input from a user; and
   predicting, by the control unit further based on the input, the remaining useful life.

10. The method of claim 1 further comprising detecting, by the control unit based on the thermal aging curve and the heating cable's current location on the thermal aging curve, damage to the heating cable.

11. A method of tracking thermal age of a heating cable of an electrical system, the heating cable having a cable type, and the electrical system including a control unit for monitoring the heating cable, the method comprising:
receiving, by the control unit, a cable signal generated by passing a line current through the heating cable;
extracting, from the cable signal by the control unit, spectral information comprising a line frequency, one or more harmonic frequencies of the line frequency, and an amplitude component for each of the line frequency and harmonic frequencies;
calculating, by the control unit, one or more measured functional dependencies of one or more pairs of corresponding amplitude components of the harmonic frequencies, wherein one or more of the measured functional dependencies is a temperature-dependent functional dependence; and
determining, by the control unit, the thermal age of the heating cable by:
determining an ambient temperature of the heating cable at the time of collecting the cable signal;
comparing one or more of the measured functional dependencies to characterization data of the cable type, the characterization data comprising one or more stored functional dependencies of harmonic frequency amplitudes and a thermal aging curve having locations to which the stored functional dependencies correlate; and
comparing the temperature-dependent functional dependence to its associated stored ratio that correlates to the determined ambient temperature.

12. The method of claim 11, wherein the cable signal is collected at an ambient temperature, the method further comprising determining, from a plurality of the measured functional dependencies, the ambient temperature.

13. A method of tracking thermal age of a heating cable of an electrical system, the heating cable having a cable type, and the electrical system including a control unit for monitoring the heating cable, the method comprising:
obtaining, by the control unit, a thermal aging curve and a subset of stored functional dependencies of harmonic frequency amplitudes that correlate to locations on the thermal aging curve, wherein the thermal aging curve is generated by:
artificially thermally aging a sample cable of the cable type;
while thermally aging the sample cable, at discrete time intervals:
collecting a test cable signal generated by passing a line current through the sample cable;
extracting, from the test cable signal, spectral information comprising a line frequency, one or more harmonic frequencies of the line frequency, and an amplitude component for each of the line frequency and harmonic frequencies; and
calculating the one or more stored functional dependencies of harmonic frequency amplitudes from the test cable signal; and
plotting the one or more stored functional dependencies against the sample cable's thermal age at the time of collecting the test cable signal to produce the thermal aging curve;
collecting, by the control unit, a cable signal generated by passing a line current through the heating cable;
extracting, from the cable signal by the control unit, spectral information comprising a line frequency, one or more harmonic frequencies of the line frequency, and an amplitude component for each of the line frequency and harmonic frequencies;
calculating, by the control unit, one or more measured functional dependencies of one or more pairs of the harmonic frequency amplitudes; and
comparing, by the control unit, one or more of the measured functional dependencies to one or more of the stored functional dependencies to determine the heating cable's current location on the thermal aging curve.

14. The method of claim 13, wherein the test cable signal is collected at one or more known ambient temperatures.

15. A system for monitoring a deployed heating cable having a cable type, the system comprising:
a detection circuit in electrical communication with the heating cable, the detection circuit configured to collect a cable signal of the deployed heating cable, the cable signal being generated by passing a line current through the deployed heating cable;
a control unit in electrical communication with the detection circuit, the control unit storing a thermal aging curve of an exemplary heating cable having the cable type, the thermal aging curve describing a test signal of the exemplary heating cable collected during an artificial aging of the exemplary heating cable, the control unit being configured to:
receive the cable signal;
determine, from the cable signal, a line frequency of the line current;
extract, from the cable signal, spectral information comprising a first amplitude of the cable signal at a first harmonic frequency of the line frequency and a second amplitude of the cable signal at a second harmonic frequency of the line frequency;
calculate a first measured functional dependency based on the first amplitude and the second amplitude;
determine from the thermal aging curve a first stored dependency between the first harmonic frequency and the second harmonic frequency, the first stored dependency based at least in part on a ratio of corresponding amplitudes of the test signal at the first harmonic frequency and the second harmonic frequency;
compare the first measured functional dependency to the first stored dependency to determine the heating cable's current location on the thermal aging curve; and
determine, based at least in part on the current location, a thermal age of the deployed heating cable.

16. The system of claim 15, wherein the control unit is located in physical proximity to the heating cable.

17. The system of claim 15, wherein the control unit is located remotely from the heating cable.

18. The system of claim 15, wherein the control unit is further configured to produce an alert if the current location of the heating cable on the thermal aging curve is beyond a threshold location on the thermal aging curve that indicates the heating cable requires replacement.

* * * * *